(12) United States Patent
Lebon et al.

(10) Patent No.: US 10,441,585 B2
(45) Date of Patent: Oct. 15, 2019

(54) FORMULATIONS CONTAINING NALBUPHINE AND USES THEREOF

(71) Applicant: DEBREGEAS ET ASSOCIES PHARMA, Paris (FR)

(72) Inventors: Christophe Lebon, Rouvres (FR); Pascal Suplie, Montaure (FR); David Olivier Paul, Dreux (FR)

(73) Assignee: DEBREGEAS ET ASSOCIES PHARMA, Paris (FR)

( * ) Notice: Subject to any disclaimer, the term of this patent is extended or adjusted under 35 U.S.C. 154(b) by 4 days.

(21) Appl. No.: 15/170,033

(22) Filed: Jun. 1, 2016

(65) Prior Publication Data

US 2016/0271124 A1 Sep. 22, 2016

Related U.S. Application Data

(63) Continuation of application No. 13/810,358, filed as application No. PCT/FR2011/051929 on Aug. 18, 2011, now abandoned.

(30) Foreign Application Priority Data

Aug. 20, 2010 (FR) .................................... 10 56689

(51) Int. Cl.

| A61K 31/48 | (2006.01) |
|---|---|
| A61K 31/485 | (2006.01) |
| A61K 9/20 | (2006.01) |
| A61K 9/28 | (2006.01) |
| A61K 9/00 | (2006.01) |
| A61K 9/16 | (2006.01) |
| A61K 9/50 | (2006.01) |

(52) U.S. Cl.
CPC .......... *A61K 31/485* (2013.01); *A61K 9/0053* (2013.01); *A61K 9/2009* (2013.01); *A61K 9/2013* (2013.01); *A61K 9/2018* (2013.01); *A61K 9/2027* (2013.01); *A61K 9/2866* (2013.01); *A61K 9/1676* (2013.01); *A61K 9/5047* (2013.01); *A61K 9/5078* (2013.01)

(58) Field of Classification Search
CPC .. A61K 31/485; A61K 9/0053; A61K 9/2018; A61K 9/2866

See application file for complete search history.

(56) References Cited

U.S. PATENT DOCUMENTS

| 4,282,215 A | 8/1981 | Dudzinski et al. | |
|---|---|---|---|
| 4,366,159 A * | 12/1982 | Magruder | A61K 31/485 514/282 |
| 4,477,457 A * | 10/1984 | Smith, Jr. | A61K 31/485 514/289 |
| 2002/0013357 A1* | 1/2002 | Nadkarni | A61K 9/145 514/406 |
| 2002/0164371 A1* | 11/2002 | Ting | A61K 9/209 424/468 |
| 2008/0207667 A1* | 8/2008 | Rhame | A61K 31/485 514/282 |
| 2009/0030026 A1 | 1/2009 | Baichwal et al. | |
| 2009/0060871 A1* | 3/2009 | Voronkov | A61K 9/2027 424/85.4 |
| 2010/0183687 A1* | 7/2010 | Cox | A61K 9/146 424/400 |
| 2011/0077238 A1* | 3/2011 | Leech | A61K 31/137 514/220 |

OTHER PUBLICATIONS

Rudnic, E.M.; Schwartz, J.B. Remington: The Science and Practice of Pharmacy, 21st Edition. 2005, Ch 45, pp. 889-928.*
Jarosz, P.J. et al. "Effect of Lubricants on Tensile Strengths of Tablets" Drug Development and Industrial Pharmacy 1984, 10 (2), 259-273 (Abstract only).*
Rudnic, E.M.; Schwartz, J.B. Remington: The Science and Practice of Pharmacy, 21st Edition. 2005, Ch 45, pp. 889-928 (Year: 2005).*
Balasubramaniam, J. et al. Pharmaceutical Technology Europe vol. 21, Issue 9, Sep. 1, 2009 (http://www.pharmtech.com/influence-superdisintegrant-choice-rate-drug-dissolution) pp. 1-7 (Year: 2009).*
"Pharmainfo" Tablet Disintegrants (http://www.pharmainfo.net/tablet-disintegrants) accessed Jan. 19, 2016. (Year: 2016).*
"Tablettose" (http://www.meggle-pharma.com/index.php/en/products-and-services/products/product-overview/tablettose-80-agglomerated-) available Feb. 7, 2011. (Year: 2011).*
Buhler, V. "Polyvinylpyrrolidone Excipients for Pharmaceuticals: Povidone, Crospovidone and Copovidone" 2005, pp. 1-254. (Year: 2005).*
Carter, J.C. "The Role of Disintegrants in Solid Oral Dosage Manufacturing" (http://www.carterpharmaceuticalconsulting.com/articles/The-role-of-disintergrants.html) 2006, pp. 1-3 (Year: 2006).*
Feb. 1, 2016 Office Action issued in U.S. Appl. No. 13/810,358.
"Pharmainfo" Tablet Disintegrants (http://www.pharmainfo.net/tablet-disintegrants) accessed Jan. 19, 2016.
"Tablettose" (http://www.meggle-pharma.com/index. php/en/products -and-services/products/product-overview/tablettose-80-agglomerated-) available Feb. 7, 2011.
Buhler, V. "Polyvinylpyrrolidone Excipients for Pharmaceuticals: Povidone, Crospovidone and Copovidone" 2005, pp. 1-254.
Rubinstein, M.H.; Rughani, J.M. "The Effect of Four Tablet Binders on the Bioavailability of Frusemide From 40MG Tablets" Drug Dev. Ind. Pharm. 1978, 4 (6), 541-553.
Aungst et al. "Oral and Rectal Nalbuphine Bioavailability: First-Pass Metabolism in Rats and Dogs" Biopharm & Drug Disposition, 1985, 6, 413-321.
Lo et al., "The Disposition and Bioavailability of the Intravenous and Oral Nalbuphine in Healthy Volunteers," J. Clin. Pharmacol, 1987, vol. 27, pp. 866-873.
International Search Report issued in International Patent Application No. PCT/FR2011/051929 dated Mar. 20, 2012.
Jul. 28, 2015 Office Action issued in U.S. Appl. No. 13/810,358.
Aug. 15, 2014 Office Action issued in U.S. Appl. No. 13/810,358.

* cited by examiner

*Primary Examiner* — Andrew S Rosenthal
(74) *Attorney, Agent, or Firm* — Oliff PLC

(57) ABSTRACT

Immediate release, oral, pharmaceutical formulation comprising nalbuphine or a pharmaceutically acceptable salt thereof, and at least one hydrophilic granulation carrier, one hydrophilic binder and one lubricant.

10 Claims, 1 Drawing Sheet

FORMULATIONS CONTAINING NALBUPHINE AND USES THEREOF

The subject-matter of the present invention is a pharmaceutical formulation containing nalbuphine and the use thereof for the treatment of pain.

Pain is a very common disorder and is one of the symptoms that is most frequently given therapeutic treatment.

Millions of individuals suffer continually from recurrent pain without receiving treatment that is fully satisfactory in terms of improvement in symptoms.

Morphine derivatives have been widely used in the past to treat pain and their use has been substantially increased over the last ten years.

Nalbuphine is a semi-synthetic opiate derivative of receptor κ-agonist and receptor μ-antagonist type, belonging to the phenanthrene series. This molecule is classified by WHO under Schedule IIA. Its analgesic activity is equivalent to that of morphine and ten times greater than the activity of pentazocine.

It is also used for anaesthesia. Its other advantage lies in the lower incidence of respiratory depression and addiction compared with other opiate derivatives.

With the following properties nalbuphine is effectively an ideal analgesic: quick-acting, intense action, scarce inhibitor effect on the cardiovascular system and respiratory system, and no addictogenic effect.

However, while nalbuphine is well absorbed via intravenous route (IV), absorption via oral route is low and variable owing to strong first-pass metabolism in the liver. Therefore the forms of nalbuphine currently marketed are intended for parental, intramuscular or rectal route with the shortcomings and adverse effects associated with these routes of administration.

Various pharmaceutical compositions containing nalbuphine have been previously researched and described.

International application WO 82/03768 describes a nasal form consisting of a solution, a suspension or an ointment. No mention is made of an oral form.

International applications WO 98/0951 and WO 00/24386 describe transdermal patches of active ingredient and notably nalbuphine hydrochloride.

U.S. Pat. No. 6,680,067 concerns a controlled release GR pharmaceutical composition, in the form of an oily suspension, comprising an analgesic compound which is nalbuphine in base or salt form, in a mixture with oil for injection. This composition is characterized in that it comprises microparticles in the oil suspension, the particle size being less than 100 μm, obtained using an ultra high energy mixer allowing particles smaller than 100 microns in size to be obtained.

The Russian patent RU 02/254852 describes a solution of nalbuphine hydrochloride for injection.

International application WO 2007/025005 concerns sustained release formulations of nalbuphine or of one of the pharmaceutically acceptable salts thereof, intended for administration via oral route; this application describes compositions comprising nalbuphine or a salt thereof and a sustained release delivery system, said system comprising at least one hydrophilic compound, at least one cross-linking agent and at least one pharmaceutical diluent, or at least one hydrophilic compound, at least one cross-linking agent, at least one pharmaceutical diluent and at least one cationic cross-linking agent different from the 1st cross-linking agent or at least one hydrophilic compound, at least one cationic cross-linking agent and at least one pharmaceutical diluent.

Similarly, international application WO 2005/127683 concerns essentially sustained release formulations of nalbuphine or a pharmaceutically acceptable salt thereof, intended for administration via oral route.

One of the objects of the invention presented herein is to provide clinicians with an oral form of nalbuphine having swift action close to that of the IV form and that is sufficiently strong.

There effectively does not exist any immediate, oral formulation at the present time since it has been observed that the immediate formulations tested up until now showed low bioavailability due to the bolus effect which causes saturation of the liver enzyme system (cytochrome p 450), which accounts for the reason why intensive research is focusing rather more on developing a sustained release form.

Another difficulty with the use of an oral form of nalbuphine lies in the particularly unpleasant intense taste of the active ingredient, which prevents direct use thereof in a solution. This assumes the need to mask the taste with usual galenic artefacts (flavouring or coating) which are detrimental to the immediate release of the active ingredient.

Research has therefore turned more towards sustained release formulations.

The objective of the present invention is to provide a novel, solid, oral pharmaceutical formulation comprising nalbuphine which allows rapid solubilization and bioavailability that is equivalent to those of a solute form of nalbuphine.

The present invention therefore concerns an immediate release, oral pharmaceutical formulation comprising nalbuphine or a pharmaceutically acceptable salt thereof and at least one hydrophilic granulation carrier, one hydrophilic binder and one lubricant.

By «hydrophilic» is meant any substance soluble or dispersible in water or in a polar solvent.

In a preferred embodiment of the invention, the pharmaceutical formulation only contains nalbuphine or one of its pharmaceutically acceptable salts as an active ingredient, preferably nalbuphine hydrochloride.

The present invention follows from the unexpected finding by the inventors that an oral, pharmaceutical formulation having immediate release, comprising nalbuphine and at least one hydrophilic granulation carrier, one hydrophilic binder and one lubricant, allows good solubility to be obtained and hence bioavailability that is equivalent to that of a solution of nalbuphine for injection, administered orally. The formulation of the invention therefore has efficacy in the treatment of pain that is equivalent to that of a formulation for injection and allows the immediate release of the active ingredient for swift treatment of pain.

The present invention therefore describes an oral, immediate release formulation of nalbuphine allowing in vivo results to be obtained that are comparable with those of a nalbuphine formulation for injection in a solution that is administered orally.

The expression pharmaceutical formulation «with immediate release» comprises all pharmaceutical formulations whose rate of release and absorption is not modified, in particular without any sustained release effect through any galenic manipulation. In the present case, immediate release is achieved through the use of at least one hydrophilic granulation carrier, one hydrophilic binder and one lubricant, pharmaceutically acceptable, which do not substantially extend the release or absorption of the formulation. The expression a «immediate-release» excludes the formulations adapted for so-called «sustained», «extended» or a «controlled release». Preferably, one immediate release form is a form in which the quantity of released substance is at least 75% in forty-five minutes («Guidance for industry, dissolution testing of immediate release solid dosage forms 1997, FDA, CDER»)

Preferably, the formulation of the invention does not contain any cross-linking agent capable, in the presence of a hydrophilic compound, of forming a matrix which can be used for delayed release of the active ingredient. By crosslinking agent is meant homopolysaccharides for example, including guar gums, locust bean gums or cationic crosslinking agents.

One formulation can be characterized by its release kinetics in vitro. Preferably, an Immediate release formulation according to the invention has in vitro release kinetics equal to or greater than 80% in 45 minutes.

The expression «nalbuphine or a salt thereof» according to the invention includes nalbuphine, nalbuphine hydrochloride/HCl, the esters of nalbuphine and their pharmaceutically acceptable salts, their complexes and derivatives. Preferably, the nalbuphine of the invention is in hydrochloride form.

The term «pharmaceutically acceptable» relates to molecules and formulations which do not induce any adverse, allergic or undesired reactions when administered to a mammal, human in particular.

The formulation of the invention comprises an hydrophilic granulation carrier, an hydrophilic binder and a lubricant. Preferably the hydrophilic granulation carrier, the hydrophilic binder and the lubricant are chosen so as to allow highly rapid solubilization of the active ingredient, permitting swift treatment of pain. Preferentially the hydrophilic granulation carrier, the hydrophilic binder and the lubricant are selected so as not to modify the release of the active ingredient according to the changes in pH, which allows taking of the formulations according to the invention, independent of food intakes which may cause change in the gastric pH.

The formulations of the invention effectively lead to near a flash a release of the active ingredient.

The expression «granulation carrier» comprises all the compounds allowing granulation of the pharmaceutical formulation according to the invention.

By «granulation», is meant all the processes allowing particles of crystallized or amorphous powder to be converted to solid aggregates of greater or less resistance and greater or lesser porosity.

Preferably, the hydrophilic granulation carrier is chosen from the group comprising polyols, for example mannitol, sorbitol, maltitol or xylitol, lactose, dicalcium phosphate, a carbonate e.g. calcium, potassium, magnesium or sodium carbonate, a gluconate, a silica derivative e.g. a silicate such as magnesium aluminium silicate (Neusilin® UFL2), sugar crystals, starch derivatives, saccharose, polyvinyl pyrrolidone (PVP) or a derivative thereof, a derivative of cellulose e.g. methylcellulose, hydroxypropyl methylcellulose or carboxymethylcellulose, polyethylene glycol or one of its derivatives alone or in a mixture.

Further preferably, the hydrophilic granulation carrier of the invention is chosen from among mannitol, polyvinyl pyrrolidone or a derivative thereof, a polyol, lactose, a cellulose derivative e.g. methylcellulose, hydroxypropyl methylcellulose or carboxymethylcellulose, polyethylene glycol or a derivative thereof and a silica derivative.

In one preferred embodiment, the granulation carrier is mannitol.

The expression «at least one granulation carrier» indicates that the pharmaceutical formulation of the invention may comprise one, two, three or more different granulation carriers.

The formulation of the invention may also comprise at least one hydrophilic binder. The binder of the invention can be chosen from among gums e.g. gum arabic or tragacanth gum, gelatin, starches, maltodextrins, polyethylene glycol e.g. PEG 4000 or 6000, PVP or a derivative thereof, solutions of saccharose, glucose or sorbitol, a polyol, lactose, carbomers, a cellulose derivative e.g. methylcellulose, hydroxypropyl methylcellulose or carboxymethylcellulose.

Preferably, the binder is chosen from the group comprising PVP or a derivative thereof, a polyol, lactose, a cellulose derivative e.g. methylcellulose, hydroxypropyl methylcellulose or carboxymethylcellulose, polyethylene glycol or a derivative thereof, gums e.g. gum arabic and tragacanth, and carbomers.

Further preferably, the binder of the invention is PVP.

The expression «at least one hydrophilic binder» indicates that the pharmaceutical formulation of the invention may comprise one, two, three or more different binders.

The formulation also comprises at least one lubricant. The lubricant according to the invention may be selected from silicon dioxide, magnesium stearate, colloidal anhydrous silica, sodium stearylfumarate or talcum.

The expression «at least one lubricant» indicates that the pharmaceutical formulation according to the invention may comprise one, two, three or more different lubricants. The lubricant(s) are selected so that they do not have any influence on the kinetics of the release of the active ingredient(s).

In one preferred embodiment, the formulation comprises three different lubricants.

The formulation of the invention may contain other compounds such as at least one excipient for example. Preferably, the excipient which may be used in the formulations of the invention is chosen from among flavouring agents or taste-masking agents, sweeteners, colouring agents and disintegration agents such as polyvinylpyrrolidone. The flavouring and taste masking agents are particularly desirable in the formulations of the invention to remove or attenuate the unpleasant taste of nalbuphine.

By «flavouring agent» is meant any substance used in the pharmaceutical industry intended to be added to formulations to modify or mask the taste or smell thereof. Sweeteners may also be used that are natural or synthetic products having a sweet taste. Preferably, pharmaceutically acceptable sweeteners are used such as sugar substitutes (polyol derivatives, natural derivatives: *stevia*, etc.) and intense sweeteners (aspartam, cyclamate, saccharin etc.).

The formulation of the invention may further contain at least one film-forming agent in particular to form a cohesive coating to increase the stability of the formula or to mask the taste. Preferably, the film-forming agent is chosen from among cellulose derivatives, HPMC, polyethylene glycol derivatives, polyvinyl pyrrolidone derivatives, waxes, acrylic derivatives (for example Eudragit® L, RL, S) and carbomers. The film-forming agent is more particularly selected so as to mask the taste while not acting on the release kinetics of the active ingredient(s). The film-forming agent is preferably hydrophilic.

The formulation according to the invention represents a particular combination of excipients with which an oral release form with a «flash effect» may be obtained. This «flash effect» release allows very fast release of the active ingredient(s). Indeed, with the formulation according to the invention, the amount of release substance is at least 95% within fifteen minutes. For a conventional immediate release form, the amount of released substance is at least 75% within forty-five minutes («Guidance for industry, dissolution testing of immediate release solid dosage forms 1997, FDA, CDER»).

In one preferred embodiment, the formulation according to the invention further comprises:
- at least one disintegrating agent;
- at least one excipient.

The formulation according to the invention may be completed by excipients, for example by compression agent(s).

In some preferred embodiments, the pharmaceutical formulation of the invention comprises less than 30% by weight of nalbuphine, preferably 4 to 30% by weight of nalbuphine and further preferably 18 to 22% by weight of nalbuphine relative to the total weight of the formulation.

In some preferred embodiments, the pharmaceutical formulation according to the invention comprises at least 45% by weight of hydrophilic granulation carrier, preferably from 45 to 70% by weight, and still preferably from 55 to 65% by weight of hydrophilic granulation carrier relative to the total weight of the formulation.

In some preferred embodiments, the pharmaceutical formulation of the invention comprises less than 10% by weight of hydrophilic binder, preferably from 2 to 10% by weight and still preferably from 4 to 8% by weight of binder relative to the total weight of the formulation.

In some preferred embodiments, the pharmaceutical formulation of the invention comprises less than 10% by weight of lubricant, preferably from 0.9 to 7% by weight and still preferably from 2 to 3% by weight of lubricant relative to the total weight of the formulation.

In one other preferred embodiment of the invention, the formulation particularly comprises:
- from 4 to 30% by weight of nalbuphine,
- from 45 to 70% by weight of lactose,
- from 2 to 10% by weight of PVP; and
- from 0.9 to 7% by weight of at least one lubricant, completed with excipients.

The pharmaceutical formulation of the invention is intended for oral administration. The pharmaceutical formulation of the invention is preferably in solid form. The solid forms of the invention particularly comprise tablets, granules, pellets, micro-granules, hard capsules, soft capsules, sublingual tablets, lozenges, pills, powders, sugar-coated tablets. Preferably the solid form of the invention is chosen from the group comprising tablets, granules, pellets, micro-granules, soft capsules and lozenges. The forms of the formulation according to the invention intended to be swallowed directly by the user such as soft capsules or tablets are particularly preferred. This administration mode allows sufficiently fast ingestion of the formulation without the user suffering discomfort from the unpleasant taste of nalbuphine.

The techniques used to obtain the solid form of the formulation according to the invention may consist of any methods known to those skilled in the art to obtain formulations in solid for. In particular, these methods may be chosen from among the techniques of wet and dry granulation, direct pressing, fluidized bed granulation, film-coating and spray drying.

The formulation of the invention preferably allows good nalbuphine bioavailability. By «good bioavailability», is meant that a sufficient proportion of nalbuphine contained in the formulation will effectively act in the body compared with the absorbed quantity and will provide the desired therapeutic effect.

In one particular embodiment, the invention concerns the pharmaceutical formulation such as defined above for use thereof as medicinal product in the treatment of pain, preferably in the treatment of non-chronic pain.

The advantage of immediate-release formulations according to the invention for said use is such that they allow swift treatment of pain, contrary to sustained release formulations.

The pain which can be treated with the pharmaceutical formulations of the invention may be due to any cause, for example pain generated by opioid addiction treatment, by cancer, by autoimmune diseases, by infections and by trauma, etc.

Preferably the pain treated with the formulation of the invention is generated by treatment of opioid addiction.

In one preferred embodiment, the invention concerns the pharmaceutical formulation as defined above for its use as a drug in the treatment of opioid addiction.

EXAMPLES

Figure 1:
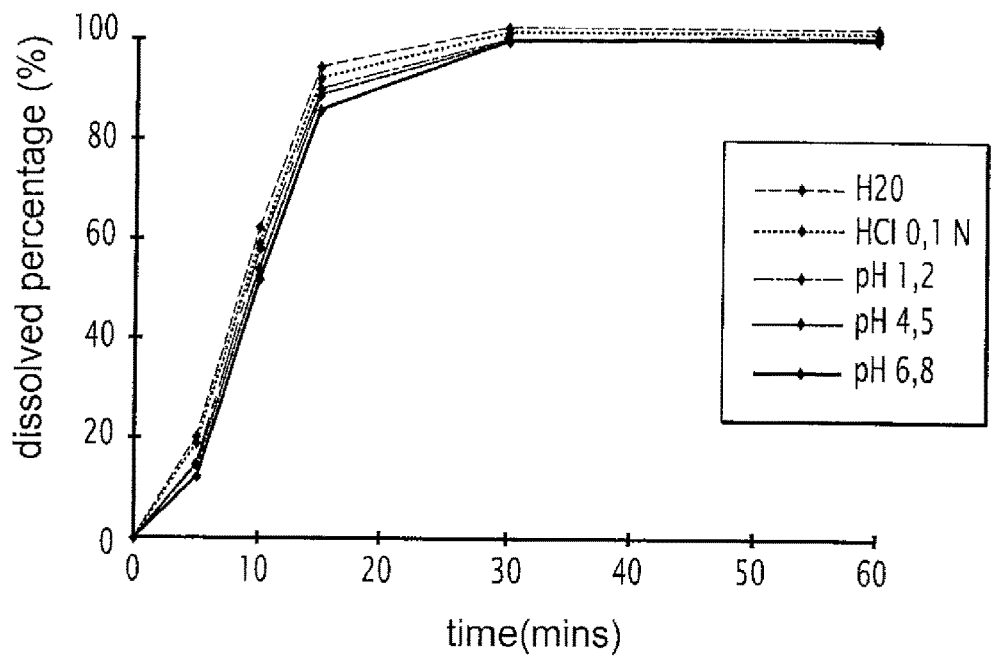
FIG. 1 illustrates the different dissolution profiles of nalbuphine versus pH.
Figure 2:
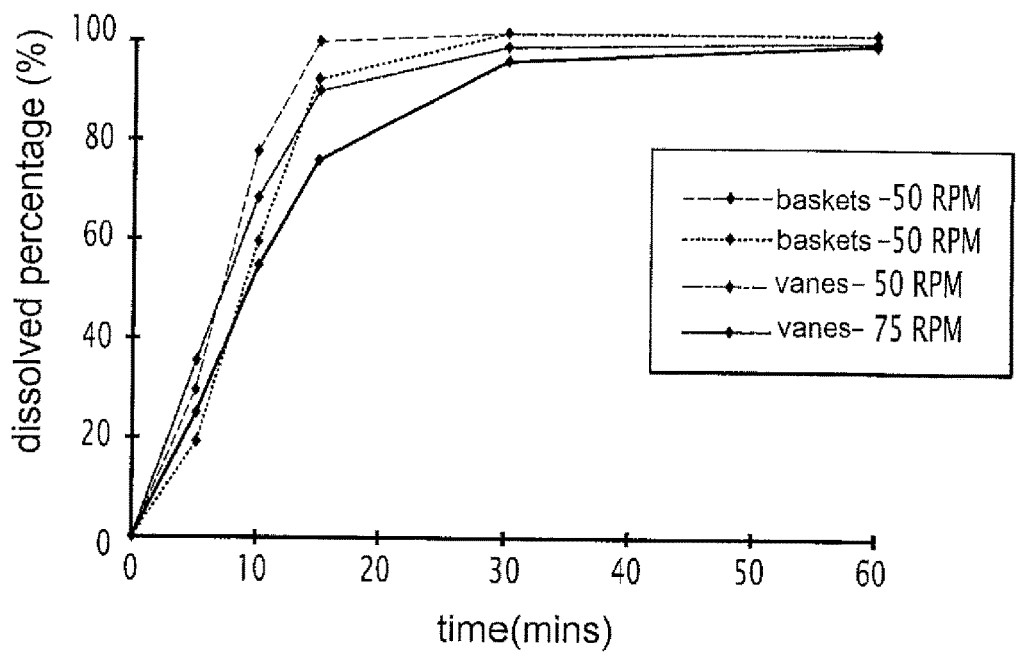
FIG. 2 illustrates the dissolved nalbuphine percentage versus time for the formulation of Example 5, according to different operating conditions.

Preparation of the Pharmaceutical Formulations in Tablet Form

The compositions and methods to prepare 9 types of formulations (Example 1, Example 2, Example 3, Example 4, Example 5, Example 6, Example 7, Example 8, and Example 9) are described below:

Example 1: 30 mg Tablets

Formula

| Raw materials | Unit (mg) | % |
|---|---|---|
| Nalbuphine/HCl | 30.00 | 4.69 |
| Povidone (PVP) | 242.01 | 37.80 |
| Mannitol (granulation carrier) | 349.49 | 54.58 |
| Crospovidone | 12.81 | 2.00 |
| Anhydrous colloidal silica | 0.64 | 0.10 |
| Sodium stearylfumarate | 3.20 | 0.50 |
| Talc | 2.14 | 0.33 |
| TOTAL | 640.29 | 100.00 |

This formulation was obtained following the protocol below:
- weighing of raw materials (scales);
- mixing nalbuphine, purified water and povidone (helix agitator);
- solubilizing and complexing the mixture (GPCG3 fluidized bed, Würster and peristaltic pump);
- coating mannitol with the mixture and drying the coated mannitol to obtain granules;
- screening the granules (mesh size 600 μm diameter, oscillating screen, mesh of 630, 500 and 400 μm);
- lubricating the granules by adding talc (Erweka mixer and 8 L cubic vessel);

mixing and lubricating the granules with mannitol, povidone, crospovidone, anhydrous colloidal silica, sodium stearylfumarate (Erweka mixer and 8 L cubic vessel);
obtaining tablets from the mixture (SVIAC RP2080 rotary press, 13 mm dies).

Example 2: 30 mg Tablets

Formula

| Raw materials | Unit (mg) | % |
|---|---|---|
| Nalbuphine/HCl | 30.00 | 18.65 |
| Talc | 4.47 | 2.70 |
| Anhydrous colloidal silica | 0.74 | 0.45 |
| Avicel PH 200 (granulation carrier) | 23.17 | 14.00 |
| Tablettose 80 (granulation carrier) | 79.44 | 48.00 |
| Povidone | 7.45 | 4.50 |
| Magnesium stearate | 0.74 | 0.45 |
| Sepifilm LP014 | 14.89 | 9.00 |
| Crospovidone | 3.72 | 2.25 |
| 96° Alcohol Surfin Pharma | / | / |
| Purified water | / | / |
| TOTAL | 320.15 | 100.00 |

This formulation was obtained following the protocol below:
weighing the raw materials (scales);
mixing the nalbuphine, talc and Tablettose® and Avicel®;
obtaining a binder solution by mixing povidone and purified water;
spraying the binder solution on the first mixture to obtain a granulate;
drying the obtained granulate in an air fluidized bed;
lubrication by adding magnesium stearate and anhydrous colloidal silica;
XL, homogenization and incorporation to the granulate direct compression of the mixture;
Preparation of the film-coating suspension: Sepifilm® LP014 and alcohol;
Film coating and then drying.

Example 3: 10 mg Tablets

Formula

| Raw materials | Unit (mg) | % |
|---|---|---|
| Nalbuphine/HCl | 10.00 | 11.86 |
| Avicel ® PH200 (microcrystalline cellulose) (granulation carrier) | 15.54 | 18.43 |
| Talc | 1.54 | 1.83 |
| Tablettose ® 80 (agglomerated α-lactose monohydrate) (granulation carrier) | 44.94 | 53.28 |
| Magnesium stearate | 0.39 | 0.46 |
| Aerosil ® 200 (silica) | 0.39 | 0.46 |
| PVP K30 | 3.85 | 4.56 |
| Sepifilm LP014 (coating) | 7.70 | 9.13 |
| TOTAL | 84.70 | 100.00 |

This formulation was obtained following the protocol given below:
weighing the raw materials (scales);
homogenizing on a cubic mixer (8 L), 5 minutes at 150 rpm, (Nalbuphine, Avicel® PH200, talc, Aerosil® 200, Tablettose® 80 and PVP K30);
lubricating the mixture with magnesium stearate for 1 minute at 150 rpm;
compressing the mixture on Korsch equipment (G009, diameter 9);
preparing the coating solution with Sepifilm LP014 and purified water on a magnetic plate;
aqueous coating of the compressed mixture on LAF GPCG 1.

Example 3-1: 50 mg Tablets

Formula

| Raw materials | Unit (mg) | % |
|---|---|---|
| Nalbuphine/HCl | 51.60 | 20.55 |
| Avicel ® ph 200 (microcrystalline cellulose) (granulation carrier) | 119.35 | 47.53 |
| PVP CL | 12.50 | 4.98 |
| Lactose | 55.30 | 22.02 |
| Magnesium stearate | 1.25 | 0.50 |
| Flavouring agent | 10.01 | 3.98 |
| Sepifilm IR 777 | 1.08 | 0.44 |
| TOTAL | 251.09 | 100.00 |

This formulation was obtained following the protocol given below:
weighing the raw materials (scales);
homogenizing on a cubic mixer (8 L), 5 minutes at 150 rpm (Nalbuphine, Avicel, lactose, PVP CL and flavouring agent);
lubricating the mixture with magnesium stearate for 1 minute at 150 rpm;
compressing the mixture on Korsch (G009, diameter 9);
preparing the coating mixture with Sepifilm IR 777, purified water and flavouring agent on a magnetic plate;
aqueous coating of the compressed mixture on LAF GPCG 1.

Example 4: 10 mg Pellets

Formula

| Raw materials | Unit (mg) | % |
|---|---|---|
| Nalbuphine/HCl | 10.00 | 1.99 |
| Taste masking agent | 146.72 | 29.20 |
| PEG 400 | 139.71 | 27.80 |
| Sucralose (sweetener) | 18.54 | 3.69 |
| Caramel flavouring | 12.84 | 2.56 |
| Neusilin UFL2 (granulation carrier) | 107.00 | 21.29 |
| Povidone K30 (PVP) | 32.61 | 6.49 |
| Sepifilm LP014 | 32.60 | 6.49 |
| Talc | 2.50 | 0.50 |
| TOTAL | 502.52 | 100.00 |

This formulation was obtained following the protocol given below:
weighing the raw materials (scales);
dispersing PEG 400, nalbuphine, sucralose, taste masking agent, caramel flavouring in ethanol (agitator);
impregnating (mixer and peristaltic pump) Neusilin UFL2 with this mixture, calibration (oscillating rotor) and drying (fluidized bed dryer, top spraying);

adding PVP 30 and purified water and granulating the mixture obtained (fluidized bed dryer, top spraying vessel);

calibrating the pellets (oscillating rotor and 800 μm mesh);

adding Sepifilm LP104 and water to coat the particles and drying (fluidized bed granulator, Würster vessel);

lubricating the coated particles with talc (cubic mixer).

Example 5: 30 mg Tablets

Formula

| Raw materials | Unit (mg) | % |
|---|---|---|
| Nalbuphine | 30.00 | 20.31 |
| PVP K30 | 9.83 | 6.65 |
| Polyplasdone XL | 3.52 | 2.38 |
| Avicel ® PH200 | 1.19 | 1.76 |
| Tablettose ® 80 | 91.85 | 62.16 |
| Aerosil ® 200 | 0.14 | 0.10 |
| Magnesium stearate | 0.71 | 0.48 |
| Talc | 2.83 | 1.92 |
| Sepifilm LP014 | 7.11 | 4.81 |
| Purified water | / | / |
| TOTAL | 147.75 | 100.00 |

This formulation was obtained following the protocol below:

weighing the raw materials (scales);

mixing the nalbuphine, talc and Tablettose® (granulation carrier);

obtaining a binder solution by mixing purified water with PVP K30;

spraying the binder solution on the first mixture to obtain a granulate;

drying the obtained granulate in an air fluidized bed;

mixing Avicel®, Aerosil® and Polyplasdone XL, homogenization and incorporation to the granulate;

lubrication by adding magnesium stearate and anhydrous colloidal silica;

direct compression of the mixture;

preparation of the film-coating suspension: Sepifilrm LP014 and purified water;

Film coating and then drying.

Example 6: Comparative Study of the Disintegration Time of the Tablets with Formulations Having Different Granulation Carrier Replacement of Tablettose 80 with Calcium Glycerophosphate

| Raw materials | Coated tablets | | | |
|---|---|---|---|---|
| | g | mg | % | mg obtained |
| Nalbuphine | 63.978 | 30.865 | 20.659 | 30.947 |
| Talc | 5.880 | 2.837 | 1.899 | 2.844 |
| calcium glycerophosphate | 190.522 | 91.913 | 61.520 | 92.157 |
| 25% PVP K30 | 20.398 | 9.840 | 6.586 | 9.867 |
| Polyplasdone XL | 8.130 | 3.922 | 2.625 | 3.932 |
| Avicel ph 200 | 4.067 | 1.962 | 1.313 | 1.967 |
| Aerosil 200 | 0.332 | 0.160 | 0.107 | 0.160 |
| Mg stearate | 1.634 | 0.788 | 0.528 | 0.790 |
| Sepifilm LP 014 | 14.750 | 7.116 | 4.763 | 7.135 |
| Purified water | 132.72 | — | — | — |
| TOTAL | 309.690 | 149.40 | 100.00 | 149.80 |

The amounts of raw materials are very close to those of the composition of Example 5. Only the granulation carrier was changed in this composition of coated tablets.

The tablets according to the composition above and tablets according to the composition of Example 5 are tested.

They are subject to constant stirring in a medium maintained at 37.0° C. (+/−0.5° C.) in a dissolution apparatus. Samples are taken, by means of a piston pump and a sample collector at 5, 10, 15, 30 and 60 minutes. These samples are then analyzed by HPLC.

The dissolution conditions are the following:

apparatus 1 USP<711> (apparatus with baskets)

speed of rotation: 50 rpm.

dissolution medium: HCl 0.1N volume: 500 Ml.

Test sample: a 30 mg tablet.

The disintegration time for these coated tablets is greater than 8 hours 30 mins.

The disintegration time under the same operating conditions for Example 5 is located between 5 and 8 minutes.

Example 7: Study of Dissolution in Media with Different pH

The operating conditions are identical with those used for the previous comparative study.

During this study, several media with different pH were tested: HCl 0.1N, at pH 1.2, 4.5 and 6.8 (FIG. 1).

It is seen that the pH and the nature of the medium have practically no influence on the dissolution profile of the formulation.

Example 8: Solubility of the Formulations

The increase in bioavailability of the formulations is estimated in relation to the dissolution of the pharmaceutical form.

An immediate release form is a form in which the quantity of released substance is at least 75% in forty-five minutes («Guidance for industry, dissolution testing of immediate release solid dosage forms 1997, FDA, CDER»). The dissolution profiles of the different formulations are obtained by dissolution measurements.

For this purpose, dissolution equipment equipped with impellers is used. The formulations are subjected to constant agitation at 50 rpm in a vessel containing 500 ml purified water and held at 37° C.

Samples are taken at predetermined times, for 1 hour and then HPLC analyzed with ultraviolet detection at a wavelength of 285 nm.

Formulation of Example 1

| Time (min) | 5 | 15 | 30 | 45 |
|---|---|---|---|---|
| % dissolution Nalbuphine | 84 | 96 | 97 | 97 |

Formulation of Example 3

| Time (min) | 5 | 15 | 30 |
|---|---|---|---|
| % dissolution Nalbuphine | 84 | 93 | 96 |

Formulation of Example 4

| Time (min) | | 5 | 10 | 15 |
|---|---|---|---|---|
| % dissolution | Nalbuphine | 97 | 99 | 98 |

As shown by the results of these experiments, the different formulations presented were specifically developed to obtain very fast dissolution times, conforming to the definition.

Example 9: Pharmacokinetic Study

An open Phase I trial, two arms, was conducted with the following formulations:

oral formulation of Example 1 (30 mg tablets)

intravenous form (IV) of nalbuphine administered orally

A trial was conducted comprising the administration of a single dose to 8 fasting, healthy male volunteers (4 volunteers per arm). Different parameters were measured: Tmax (time after which the maximum quantity of formulation is dissolved), Cmax (maximum quantity of dissolved formulation) and AUC (concentration/time, area under curve). AUC is calculated by both arithmetic and geometric means. Geometric mean is used to moderate extreme values and is more accurate from a statistical point of view. AUC ratio between experimental and reference products are presented taking into account real administered dose, or adjusted to correct the dose difference (normalized).

In the tables, AUCinf means AUC extrapolated to infinity, and AUCt means AUC truncated at the last time of plasmatic measurement in the PK study. The following results were obtained:

TABLE 1

Tmax based on mean values

| Formulation | Tmax (h) |
|---|---|
| 30 mg solid oral form of Example 1 | 1.25 |
| 30 mg oral solution (for comparison) IV form administered per os | 0.75 |

It is ascertained that Tmax is slightly time-shifted for the solid oral form according to the invention compared with the liquid solution of nalbuphine.

TABLE 2

Pharmacokinetic parameters, arithmetic mean value

| Formulation | Cmax (ng/mL) | Tmax (h) | AUCt (ng/mL * h) | AUCinf (ng/mL * h) |
|---|---|---|---|---|
| 30 mg solid oral form of Example 1 | 7.91 | 1.21 | 30.93 | 38.08 |
| 30 mg oral solution (for comparison) IV form administered per os | 9.34 | 0.71 | 33.06 | 39.07 |

It is ascertained that, aside from the slight difference for Tmax, the pharmacokinetic parameters are comparable for the solid form of the invention and for the oral solution.

TABLE 3

Relative Bioavailability (based on dose-normalized, arithmetic mean value)

| Formulation | Cmax ratio | AUCt ratio | AUCinf ratio |
|---|---|---|---|
| 30 mg solid oral form of Example 1/ 30 mg oral solution (for comparison) | 0.85 | 0.94 | 0.97 |

TABLE 4

Pharmacokinetic parameters, geometric mean value

| Formulation | Cmax (ng/mL) | AUCt (ng/mL * h) | AUCinf (ng/mL * h) |
|---|---|---|---|
| 30 mg solid oral form of Example 1 | 6.72 | 26.22 | 31.80 |
| 30 mg oral solution (for comparison) | 8.63 | 29.72 | 34.47 |

TABLE 5

Relative bioavailability (based on dose-normalized geometric mean value)

| Formulation | Cmax ratio | AUCt ratio | AUCinf ratio |
|---|---|---|---|
| 30 mg solid oral form of Example 1/ 30 mg oral solution (for comparison) | 0.78 | 0.88 | 0.92 |

These data indicate that the tested oral form shows bioavailability close to that observed for the IV form administered orally; a slight difference is observed for Tmax but the release obtained is very rapid and this is not detrimental to the desired therapeutic effect.

Example 10: Comparative Study Versus Reference Oral Solution

The data from the preceding study were compared with data given in the bibliography. Based on the linearity of the administered dose, the following values are obtained:

TABLE 6

Pharmacokinetic parameters (arithmetic means - dose normalized to 30 mg)

| Formulation | Cmax (ng/mL) | AUCt (ng/mL * h) | AUCinf (ng/mL * h) |
|---|---|---|---|
| 30 mg solid oral form of Example 1 | 7.91 | 30.93 | 38.08 |
| 30 mg oral solution of nalbuphine | 6.88 | 30.93 | 34.25 |

TABLE 7

Relative bioavailability (based on arithmetic mean value - dose normalized to 30 mg)

| Formulation | Cmax ratio | AUCt ratio | AUCinf ratio |
|---|---|---|---|
| 30 mg solid oral form of Example 1/ 30 mg oral solution (for comparison) | 1.15 | 1.00 | 1.11 |

TABLE 8

| Formulation | Pharmacokinetic parameters (geometric mean values - dose normalized to 30 mg) | | |
|---|---|---|---|
| | Cmax (ng/mL) | AUCt (ng/mL * h) | AUCinf (ng/mL * h) |
| 30 mg Solid oral form of Example 1 | 6.72 | 26.22 | 31.80 |
| 30 mg Oral solution of nalbuphine | 6.24 | 28.15 | 31.57 |

TABLE 9

| Relative bioavailability (based on geometric mean value normalized to a dose of 30 mg) | | | |
|---|---|---|---|
| 30 mg solid oral form of Example 1/ 30 mg oral solution (for comparison) | 1.08 | 0.93 | 1.01 |

On reasoning with geometric mean values, the bioavailability stated for the oral solution of nalbuphine is comparable with that observed for the solid form.

Example 11: Comparative Study Versus Oral Reference Solution

A second phase I study, with a single arm, was conducted on the oral formulation of Example 2 (30 mg tablets).

This study was completed by administering a single dose of 30 mg of nalbuphine to 12 male healthy volunteers with empty stomachs. Different parameters were measured: Tmax (time after which the maximum quantity of formulation is dissolved), Cmax (maximum quantity of dissolved formulation) and AUC (area located under the concentration versus time curve).

The observed data were compared with the data obtained during the study of example 9 for the intravenous form (IV) of nalbuphine administered orally.

| Formulation | Cmax (ng/mL) | Tmax (ng/mL) | AUCinf (ng/mL * h) |
|---|---|---|---|
| 30 mg oral solid form of Example 2 | 12.2 | 2.63 | 38.1 |
| 30 mg oral liquid form (as a comparison) | 9.3 | 3.11 | 39.1 |

Here also, the observed values are similar. It is noted that the values of Cmax and of AUC are close to each other. Tmax is shorter for the formulation according to example 2.

The invention claimed is:

1. An immediate release, oral pharmaceutical formulation comprising in percentage by weight:
   20.55% nalbuphine/HCl,
   22.02% lactose,
   47.53% microcrystalline cellulose,
   4.98% povidone,
   0.50% magnesium stearate,
   3.98% flavoring, and
   0.44% coating.

2. The pharmaceutical formulation of claim 1, wherein the formulation is in a form of a tablet.

3. The pharmaceutical formulation of claim 2, wherein the tablet is a 50 mg tablet.

4. A method of treating of pain, comprising:
   administering an effective amount of the pharmaceutical formulation of claim 1 to a patient in need thereof to treat pain generated by treatment for opioid addiction.

5. A method of treating pain generated by treatment for opioid addiction, comprising:
   administering the pharmaceutical formulation of claim 3 to a patient in need thereof.

6. An immediate release, oral pharmaceutical formulation comprising in percentage by weight:
   20.31% nalbuphine/HCl,
   62.16% agglomerated α-lactose-monohydrate,
   6.65% povidone,
   2.38% crospovidone,
   1.76% microcrystalline cellulose,
   0.10% silica,
   0.48% magnesium stearate,
   1.92% talc, and
   4.81% coating.

7. The pharmaceutical formulation of claim 6, wherein the formulation is in a form of a tablet.

8. The pharmaceutical formulation of claim 7, wherein the tablet is a 30 mg tablet.

9. A method of treating of pain, comprising:
   administering an effective amount of the pharmaceutical formulation of claim 6 to a patient in need thereof to treat pain generated by treatment for opioid addiction.

10. A method of treating pain generated by treatment for opioid addiction, comprising:
    administering the pharmaceutical formulation of claim 8 to a patient in need thereof.

* * * * *